US012747242B2

(12) United States Patent
List et al.

(10) Patent No.: US 12,747,242 B2
(45) Date of Patent: Sep. 29, 2026

(54) PROCESS FOR THE CATALYTIC GLYCOSYLATION OF ARENES

(71) Applicant: Studiengesellschaft Kohle gGmbH, Muelheim (DE)

(72) Inventors: Benjamin List, Muelheim an der Ruhr (DE); Carla Obradors, Antwerp (BE); Benjamin Mitschke, Muelheim an der Ruhr (DE); Miles Aukland, Muelheim an der Ruhr (DE)

(73) Assignee: Studiengesellschaft Kohle gGmbH, Muelheim (DE)

( * ) Notice: Subject to any disclaimer, the term of this patent is extended or adjusted under 35 U.S.C. 154(b) by 303 days.

(21) Appl. No.: 18/294,607

(22) PCT Filed: Jul. 26, 2022

(86) PCT No.: PCT/EP2022/070996
§ 371 (c)(1),
(2) Date: Feb. 2, 2024

(87) PCT Pub. No.: WO2023/011994
PCT Pub. Date: Feb. 9, 2023

(65) Prior Publication Data

US 2025/0115610 A1 Apr. 10, 2025

(30) Foreign Application Priority Data

Aug. 3, 2021 (EP) .................................... 21189383

(51) Int. Cl.
*C07D 487/04* (2006.01)

(52) U.S. Cl.
CPC ................................. *C07D 487/04* (2013.01)

(58) Field of Classification Search
CPC ............................. C07D 487/04; C07H 17/02
See application file for complete search history.

(56) References Cited

FOREIGN PATENT DOCUMENTS

| | | | |
|---|---|---|---|
| CN | 108530409 | A | 9/2018 |
| JP | S4926273 | A | 9/1974 |
| JP | 2000511160 | A | 8/2000 |
| WO | 1997043298 | A1 | 11/1997 |
| WO | 2016041470 | A1 | 3/2016 |

OTHER PUBLICATIONS

Eva Bokor et al., "C-Glycopyranosyl Arenes and Hetarenes: Synthetic Methods and Bioactivity Focused on Antidiabetic Potential", Chemical Reviews, vol. 117, No. 3, Jan. 25, 2017 (Jan. 25, 2017), pp. 1687-1764.
Timo von Keutz et al., "Flash Chemistry Approach to Organometallic C-Glycosylation for the Synthesis of Remdesivir", Organic Process Research & Development, vol. 25, No. 4, Apr. 16, 2021 (Apr. 16, 2021), pp. 1015-1021.
Obradors, C., et al.; "Direct and Catalytic C-Glycosylation of Arenes Expeditious Synthesis of the Remdesivir Nucleoside", Angew Chem Int Ed—2021, pp. 1-5.
JP Office Action in corresponding application JP2024-506643 dated Jun. 16, 2026.
Zarenezhad, E., et al; "A Mini Review on Discovery and Synthesis1of Remdesivir as an Effective and Promising Drug Against COVID 19", Russian Journal of Bioorganic Chemistry 2020, vol. 47, No. 3, pp. 609-621.

*Primary Examiner* — Layla D Berry
(74) *Attorney, Agent, or Firm* — Norris McLaughlin, PA

(57) ABSTRACT

The present invention refers to a process for the catalytic glycosylation of arenes which allows, amongst others, the expeditious synthesis of the nucleoside analogue GS-441524 of the antiviral prodrug remdesivir.

14 Claims, 3 Drawing Sheets

PROCESS FOR THE CATALYTIC GLYCOSYLATION OF ARENES

Figure 1:
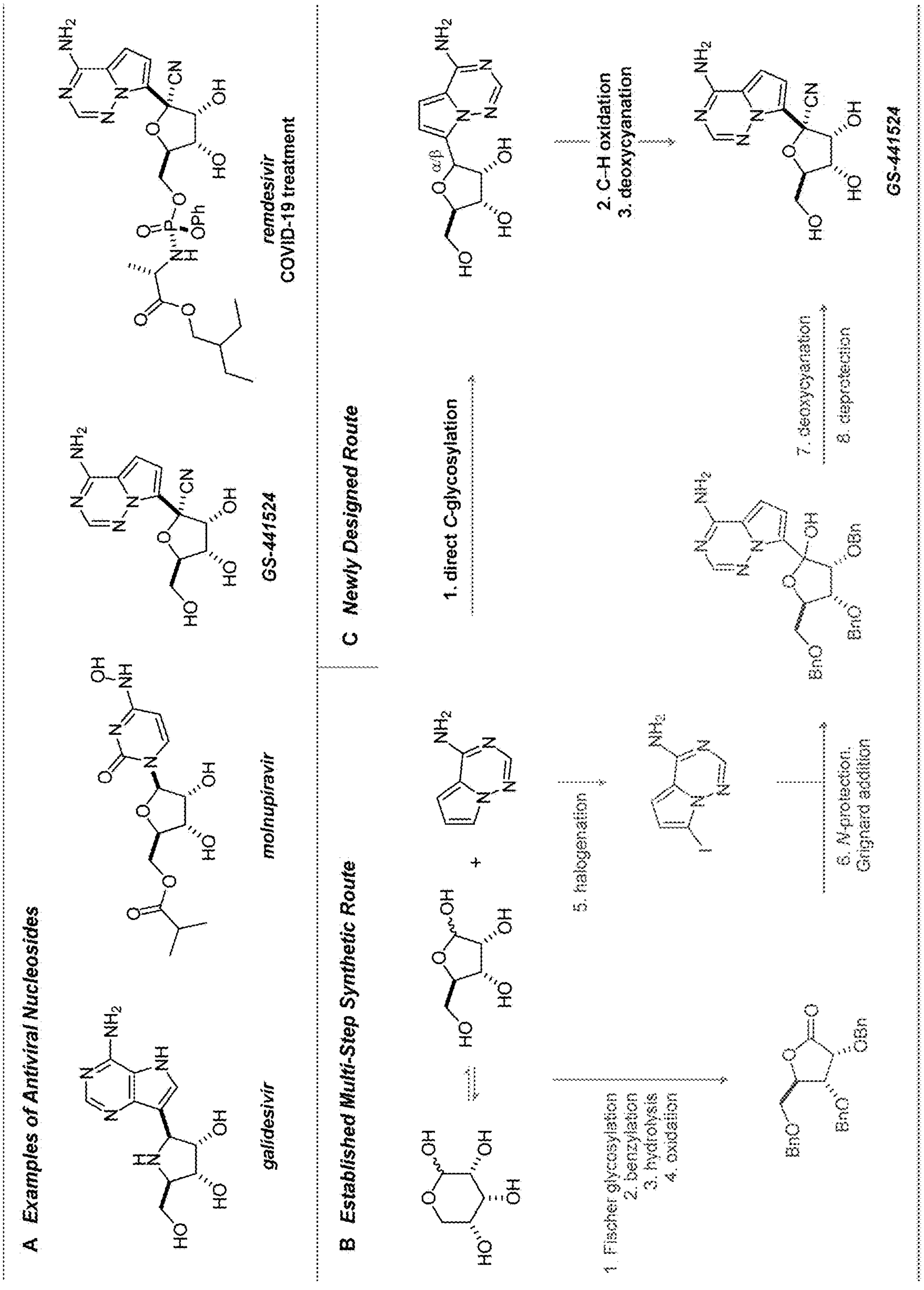

This application is a 371 of International Patent Application No. PCT/EP2022/070996, filed Jul. 26, 2022, which claims priority of European Patent Application No. 21189383.9, filed Aug. 3, 2021, the disclosures of which patent applications are hereby incorporated herein by reference.

The present invention refers to a process for the catalytic glycosylation of arenes which allows, amongst others, the expeditious synthesis of the nucleoside analogue of the antiviral prodrug remdesivir. Said nucleoside analogue antiviral drug was developed by Gilead Sciences and was named GS-441524. This is the main plasma metabolite of the antiviral prodrug remdesivir and has a half-life of around 24 hours in human patients.

Since early 2020, scientists have strived to find an effective solution to fight SARS-CoV-2, especially by developing reliable vaccines that inhibit the spread of the disease and repurposing drugs for combatting its effects on the human body. The antiviral prodrug remdesivir is still the most widely used therapeutic during the early stage of infection. However, the current synthetic routes rely on the use of protecting groups, air-sensitive reagents, and cryogenic conditions.

Society has witnessed the striking effect of applied and basic science on restraining the impact of SARS-CoV-2. This outbreak has been tackled especially intensely from the pharmaceutical sector in terms of small-molecule therapeutics, vaccinations and biomedical devices. The pandemic has also driven a global effort to repurpose existing drugs to enable a rapid and targeted response. Remdesivir (Veklury) is an antiviral prodrug that was originally evaluated in clinical trials to fight the Ebola virus and, although showing somewhat mixed results against COVID-19, it is still the most widely used treatment during the early stage of infection.

Consequently, there is a need for an improved process for preparing antiviral nucleosides.

A review in CHEMICAL REVIEWS, VOL. 117, pages 1687-1764, 2017, discloses a single example of a direct C-glycosylation of an arene compound with a monosaccharide in the presence of a Lewis acid catalyst without protection of the hydroxyl groups. No further details can be derived from said disclosure.

The inventors therefore focused on the development of a straightforward addition of arenes and (hetero)arenes to unprotected monosaccharides. Here, the inventors found a silylium-catalyzed and completely stereoselective C—C bond formation that yields the ring-opened polyols, which can be selectively cyclized to provide either the kinetic α-furanose or the thermodynamically favored β-anomer. The method expedites the synthesis of remdesivir precursor GS-441524 after subsequent Mn-catalyzed C—H oxidation and deoxycyanation.

In a first aspect, the present invention is directed to a process for a glycosylation of an arene wherein a monosaccharide is reacted with a silylating agent for introducing one or more silyl groups to the monosaccharide in the presence of a Lewis acid catalyst and with an aromatic hydrocarbon selected from arenes or heteroarenes, each optionally bearing one or more substituents, followed by removal of the one or more silyl groups to yield a nucleoside analogue In the inventive process, the monosaccharide is preferably selected from tetroses, pentoses, hexoses and any deoxy form thereof, the monosaccharide is more preferably selected from ribose or deoxyribose.

In the inventive process, the silylating agent can be selected from hydrosilanes, allylsilanes, methallylsilanes, arylsilanes, trifluoromethylsilanes, benzylsilanes, disilazanes, silyl halides, silyl cyanides, silyl azides, silyl phosphites, silyl ketene acetals, bis(silyl)acetamides, in particular tri-($C_1$ to $C_6$-alkyl)-substituted silyl compounds, preferably bis(silyl)acetamides, more preferably (N,O-Bis(trimethylsilyl)trifluoroacetamide, and is preferably used to transfer a tri-($C_1$ to $C_6$-alkyl)-substituted silyl group to each hydroxyl group of the monosaccharide in the hemiacetal form, i.e. in the form of a furanose or a pyranose. In the inventive process, BSTFA (N,O-Bis(trimethylsilyl)trifluoroacetamide is the preferred silylating agent which can also serve as solvent for the reactants.

The reaction conditions are not very critical and reaction temperature and reaction pressure can be adapted to the reaction partners. A solvent for the reactants can be used and can be selected from a non-polar to polar aprotic organic solvent such as pentane, hexane, benzene, toluene, xylenes, dichloromethane, 1,2-dichloroethane, tetrahydrofuran, diethyl ether, 1,4-dioxane, ethyl acetate, dimethylformamide, acetonitrile. Preferably, the reaction is carried out as a one pot reaction under ambient temperature up to a slightly elevated temperature of 50° C. to 70° C., and under atmospheric pressure.

The Lewis acid catalyst is not particularly limited and can be selected from boron trifluoride etherate, calcium(II) bis(trifluoromethanesulfonimide), aluminium chloride, iron(III) chloride, tin(IV) chloride, indium(III) trifluoromethanesulfonate, bismuth(III) trifluoromethanesulfonate, rare-earth metal trifluoromethanesulfonates, zirconocene dichloride, tritylium tetrafluoroborate, silyl trifluoromethanesulfonates, silyl perchlorates, silyl bis(trifluoromethanesulfonyl)imide, silyl disulfonimides (DSIs), silyl binaphthyl-allyl-tetrasulphones (BALTs), silyl imidodiphosphorimidates (IDPis), N,N'-bis(trifluoromethanesulfonyl)phosphoramidimidates (PADIs). In the inventive process, TMSOTf (trimethylsilyl)trifluoromethanesulfonate is a preferred Lewis acid.

The aromatic hydrocarbon can be selected from arenes containing one to four aromatic rings, each ring optionally being substituted by one or more heterosubstituents, or heteroarenes containing 1 up to 4 rings and containing 1 to 4 heteroatoms, each ring optionally being substituted by one or more heterosubstituents, and is further defined below. The preferred arenes or preferred heteroarenes, respectively, can be selected from anisoles, anilines, pyrroles, furans, thiophenes, oxazoles, thiazoles, isoxazoles, isothiazoles, imidazoles, triazoles, oxadiazoles, tetrazoles, pyrazoles, azepines, pyridines, pyridazines, pyrimidines, pyrazines, oxazines, thiazines, triazines, each optionally being substituted by one or more heterosubstituents.

In a second aspect, for providing the reactive drug GS-441524, the nucleoside analogue wherein the monosaccharide is ribose and the heteroarene is pyrrolo[2,1-f][1,2,4]triazin-4-amine and which is obtainable according to the inventive process, can be further treated with a protecting agent for the hydroxyl groups, the obtained protected nucleoside analogue is treated with an oxidizing agent to introduce a hydroxyl group on the anomeric carbon atom and the obtained reaction product having the hydroxyl group on the anomeric carbon atom is treated with a cyanating agent to replace the hydroxyl group on the anomeric carbon atom by a nitrile group which reaction product is finally treated with a deprotecting agent to remove the protecting groups from the hydroxyl groups on the ribose moiety.

The protecting agent for the hydroxyl groups of the ribose moiety can be selected from alkyl halides, alkyl carboxylic acid anhydrides, aryl carboxylic acid anhydrides, alkyl carboxylic acid chlorides, aryl carboxylic acid chlorides, silyl halides, bis(silyl)acetamides, silyl trifluoromethanesulfonates, acetone, alkyl chloromethyl ethers, 2-(silyl) ethoxy chloromethyl ethers, and is preferably acetic anhydride or benzoic anhydride.

After protecting the hydroxyl groups, the protected nucleoside analogue is treated with an oxidizing agent in a non-polar aprotic organic solvent for introducing an hydroxyl group at the anomeric carbon atom of the ribonucleoside. Preferably, the oxidizing agent is iodosyl benzene in the presence of Mn(TPP)Cl ((5,10,15,20-Tetraphenyl-21H,23H-porphine manganese(III) chloride) as catalyst.

In the next reaction step, the oxidized ribonucleoside as the obtained reaction product is treated with a cyanating agent, which is selected from silyl cyanides, alkali metal cyanides, preferably trimethyl silyl cyanide (TMSCN), in the presence of a strong acid as catalyst such as bis(trifluoromethane)sulfonimide in a non-polar aprotic organic solvent whereby a mixture of the α:β diastereomers is obtained, wherein the α-diastereomer (2R,3R,4R,5R)-2-(4-acetamidopyrrolo[2,1-f][1,2,4]triazin-7-yl)-5-(acetoxymethyl)-2-cyanotetrahydro-furan-3,4-diyl diacetate, is obtained as major product. Preferably, the reaction is carried out at temperatures of up to 0° C. and under atmospheric pressure.

In the next reaction step, the mixture of the α:β diastereomers is treated with a base, selected from alkali metal alcoholates, alkali metal carbonates, preferably sodium methanolate, preferably in an aliphatic alcohol such as methanol, ethanol or iso-propanol, to remove the acetate protective groups whereby a single α-diastereomer (2R,3R,4S,5R)-2-(4-aminopyrrolo[2,1-f][1,2,4]triazin-7-yl)-3,4-dihydroxy-5-(hydroxymethyl)tetrahydro-furan-2-carbonitrile is obtained.

In the context of the present invention, the following definitions are used to define the elements and groups as used in the claims and specification.

Definitions

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and acyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (acyclic, substituted, unsubstituted, branched or unbranched) having 1-6 carbon atoms.

As used herein, "alkyl" refers to a radical of a straight-chain, cyclic or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

"Aromatic hydrocarbon or arene or aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaromatic hydrocarbon or heteroarene or heteroaryl" refers to a radical of a 5-18 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen, and sulfur ("5-18 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

An atom, moiety, or group described herein may be unsubstituted or substituted, as valency permits, unless otherwise provided expressly. The term "optionally substituted" refers to substituted or unsubstituted.

Alkyl, aryl, and heteroaryl groups are optionally substituted (e.g., "substituted" or "unsubstituted" alkyl, "or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. For purposes of this invention, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary substituents include, but are not limited to, halogen, —CN, $—NO_2$, $—N_3$, $—SO_2H$, $—SO_3H$, —OH, —OR, $—ON(R)_2$, $—N(R)_2$, $—N(R)_3^+X^-$, —SH, —SR, —SSR, —C(=O)R, $—CO_2H$, —CHO, $—C(OR)_3$, $—CO_2R$, —OC(=O)R, $—OCO_2R$, $—C(=O)N(R)_2$, —OC (=O)N(R)$_2$, —NRC(=O)R, —NRCO$_2$R, —NRC(=O)N(R)$_2$, —C(=NR)R, —C(=NR)OR, —OC(=NR)R, —OC(=NR)OR, —C(=NR)N(R)$_2$, —OC(=NR)N(R)$_2$, —NRC(=NR)N(R)$_2$, —C(=O)NRSO$_2$R, —NRSO$_2$R, —SO$_2$N(R)$_2$, —SO$_2$R, —SO$_2$OR, —OSO$_2$R, —S(=O)R, —OS(=O)R, —Si(R)$_3$, —OSi(R)$_3$—C(=S)N(R)$_2$, —C(=O)SR, —C(=S)SR, —SC(=S)SR, —SC(=O)SR, —OC(=O)SR, —SC(=O)OR, —SC(=O)R, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R groups; or two geminal hydrogens on a carbon atom are replaced with the group =O, =S, =NN(R)$_2$, =NNRC(=O)R, =NNRC(=O)OR, =NNRS(=O)$_2$R, =NR, or =NOR;

wherein each instance of R is, independently, selected from $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R groups are joined to form a 3-14 membered heterocyclyl or 5-14 membered heteroaryl ring, wherein each alkyl, alkenyl, alkynyl, carbocyclyl, heterocyclyl, aryl, and heteroaryl may have one or more substituents selected from halogen, —OH, —OR, —CN, —NO$_2$, —NR$_2$ wherein R is hydrogen or $C_{1-6}$ alkyl.

"Halo" or "halogen" refers to fluorine (fluoro, —F), chlorine (chloro, —Cl), bromine (bromo, —Br), or iodine (iodo, —I).

FIGURES AND EXAMPLES

The invention is further illustrated by the attached Figures and Examples. In the Figures, the respective Figure shows:

FIG. 1. A. Examples of nucleoside-based antivirals. B. Established sequence towards the synthesis of remdesivir. C. Design here: arylation of free D-ribose.

Figure 2:
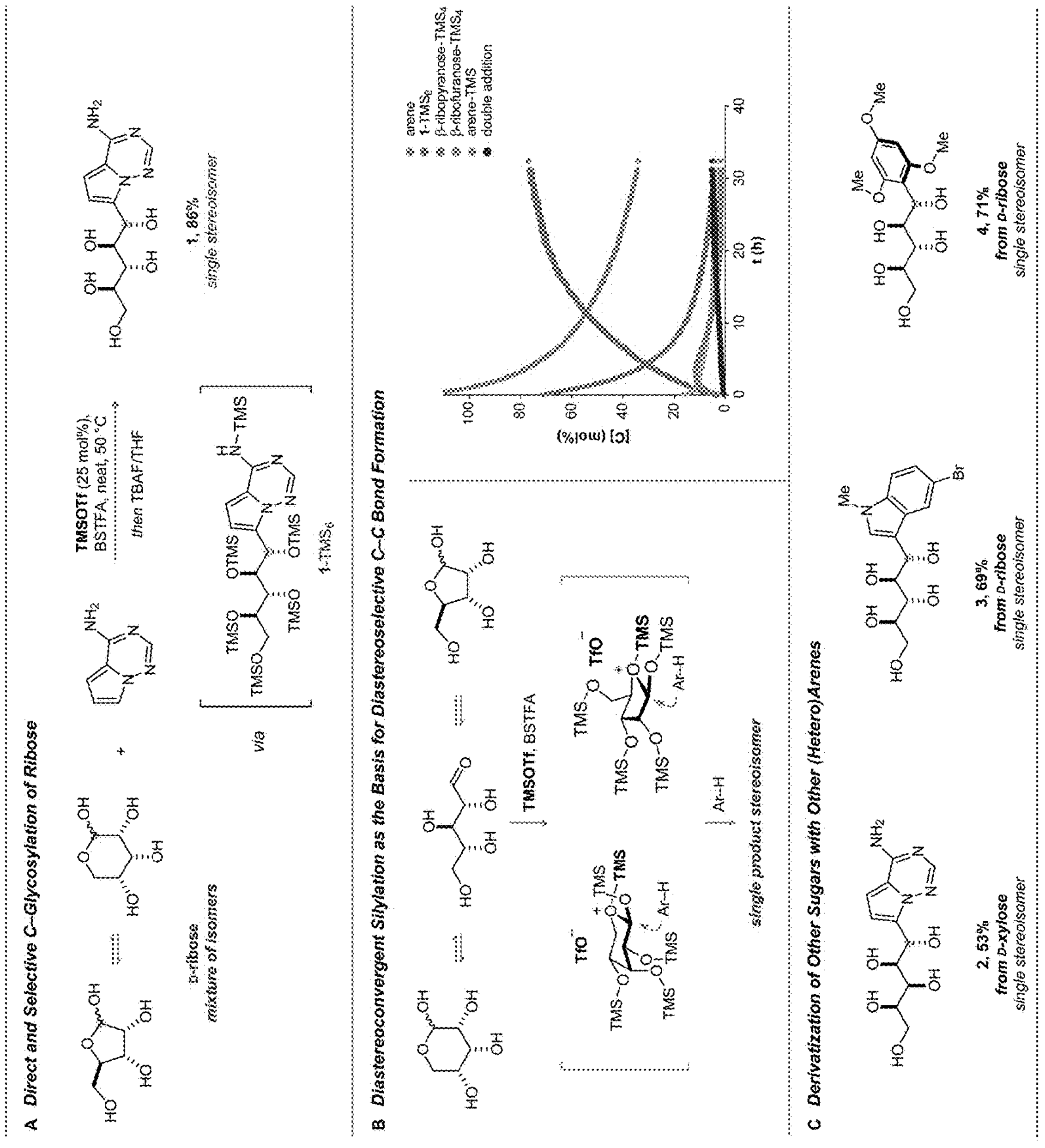

FIG. 2. A. Diastereoselective functionalization of D-ribose by transient silylation. B. Mechanistic insights on the C—C bond formation. C. Additional examples of other sugars with other (hetero)arenes.

Figure 3:
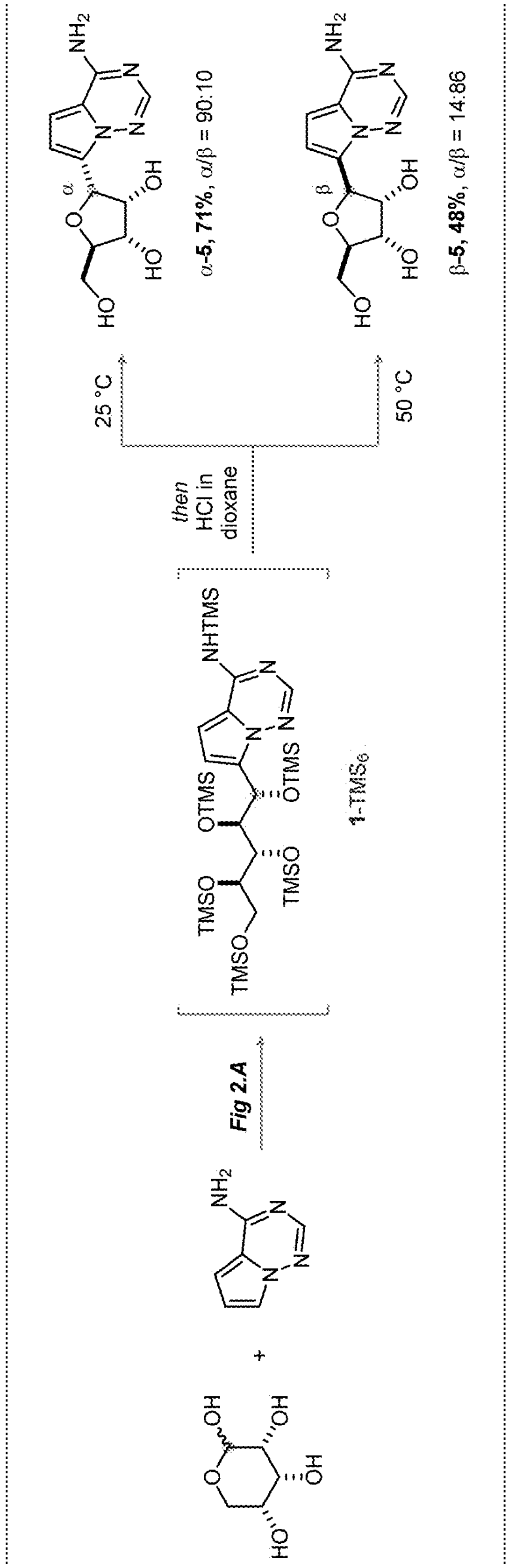

FIG. 3. Selective syntheses of both α- and β-C-glycosylated nucleosides by variation of cyclization temperature.

Figure 4:
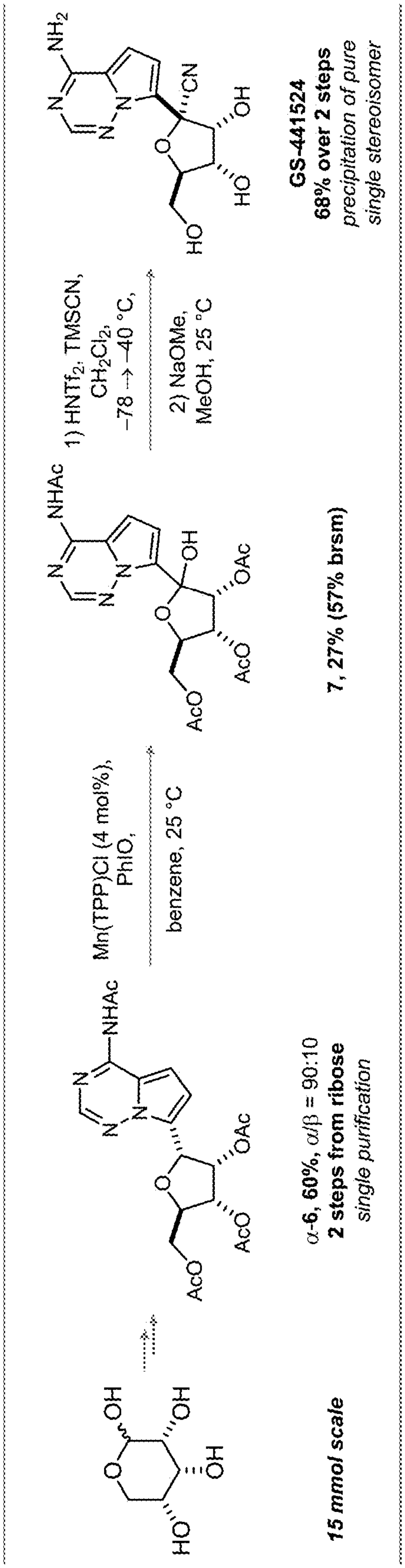

FIG. 4. Benzylic C—H oxidation and diastereoselective deoxycyanation of peracetylated ribonucleoside α-6.

As illustrated in FIG. 1, nucleotide analogs such as remdesivir are generally a class of compounds which are prominent for their RNA antiviral properties (FIG. 1A). Besides the ubiquitous presence of the monosaccharide derivative, their synthesis still relies on multi-step sequences and the use of protecting groups due to the selectivity challenges inherent in the functionalization of unprotected sugars.

In the case of remdesivir, Gilead's industrial route starts with the perbenzylated D-ribonolactone (FIG. 1B)—which is obtained in four steps from D-ribose—and requires sensitive reagents and cryogenic conditions for several of the steps involved. This context of necessity has inspired new approaches to build the heterocyclic arene and improvements to the organocatalytic asymmetric phosphoramidation to introduce the monophosphate-like side chain. However, efforts towards streamlining the construction of the core nucleoside itself have remained elusive. Recent advancements for the direct assembly of nucleosides have focused on the formation of a C-heteroatom bond in the anomeric position, whereas examples for the C—C disconnection are scarce.

The inventors aimed at the development of a new and greatly facilitated route to remdesivir featuring arylation of D-ribose by means of silylium catalysis as the key step (FIG. 1C). Here the inventors report the completely regio- and stereoselective addition of (hetero)arenes to unprotected sugars, which in turn furnishes the nucleoside intermediate in a one-pot fashion. The divergent formation of the α- or the β-anomer is achieved either by kinetic control or through a thermodynamically-driven epimerization, respectively. Finally, the new method unlocks an expedient synthesis of the remdesivir precursor GS-441524 by virtue of a selective Mn-catalyzed benzylic C—H oxidation and diastereoselective deoxycyanation.

As shown in FIG. 2, the approach of the inventors harnesses the native nucleophilicity of the heterocycle, which eliminates the requirement for prefunctionalization and the preparation of the air-sensitive organometallic reagent. Furthermore, the inventors exploit a Lewis acid-catalyzed transient silylation of the carbohydrate in order to concurrently fulfill two main purposes: in situ protection of all protic functionalities as well as selective anomeric activation (FIG. 2A). The inventors found that D-ribose is rapidly activated by catalytic TMSOTf at 25° C., which is regenerated upon protodesilylation of the innocent silicon source N,O-bis(trimethylsilyl)trifluoroacetamide (BSTFA). The key C—C bond formation occurs at 50° C. under neat conditions leading exclusively to a single linear isomer 1-TMS$_6$ in quantitative yield. During the transformation however, this dynamic mixture converges diastereoselectively to a single product. Subsequent desilylation of the crude reaction mixture with TBAF delivers the linear analog 1 in a one-pot fashion (86%), rendering the use of silicon traceless. Preliminary attempts have revealed that the method is also competent for the functionalization of alternative sugars and (hetero)arenes (FIG. 2C); here the inventors show three additional examples while a more comprehensive study is currently ongoing in our laboratory. The reaction with D-xylose also delivers product 2 as a single diastereoisomer but in slightly lower yield (53%). Moreover, addition of an indole derivative occurs in good yield at 25° C. to polyol 3 (69%). Finally, 1,3,5-trimethoxybenzene similarly enables the derivatization to compound 4 in 71% yield.

Lewis acid-catalyzed nucleophilic additions to carbohydrate derivatives are generally believed to proceed via oxocarbenium intermediates, derived from the activation of the anomeric substituent. However, this assumption is questioned here in light of the formation of a single linear product. Instead, the inventors propose a mechanism in which TMSOTf coordinates to the endocyclic oxygen atom of the sugar prior to reaction with the heterocycle leading to ring opening (FIG. 2B). Thorough NMR analysis confirmed the silylation of the sugar at 25° C., delivering a reduced amount of isomers (see Supporting Information, Figure S10-23). The inventors could indeed observe the TMS-protected ribopyranose and—furanose (77% and 21%, respectively). Only the β-anomers are present for both intermediates, in which the anomeric groups are oriented trans to the vicinal siloxy group for steric reasons (see Supporting Information, Figure S46 for DFT calculations). Consequently, successive nucleophilic substitution via an $S_N2$-type mechanism converges to the product as a single diastereoisomer. Kinetic analysis at 50° C. revealed that consumption of the arene mirrors the formation of the product, with the pyranose isomer reacting faster than the furanose. Traces of double addition were also detected.

As illustrated in FIG. 3, the inventors found that when the reaction mixture was subjected to acid treatment rather than to fluoride, the corresponding C-ribofuranosylated products are obtained (FIG. 3). Formation of the α-product 5 is achieved by performing the acid treatment at 25° C. with good yield and high diastereoselectivity (71%, α/β=90:10). In contrast, acid treatment at 50° C. leads directly to the thermodynamically favoured β-nucleoside 5 (48%, α/β=14:86). Epimerization from α- to β-could be monitored by $^{1}H$ NMR after resubmission of isolated product α-5 to HCl in dioxane at 50° C. (see Supporting Information, Figure S27).

As further illustrated in FIG. 4, a subsequent oxidative installation of the nitrile moiety was required in the context of the synthesis of the antiviral drug GS-441524. Thus, the inventors envisioned an initial C—H oxidation to furnish the stereolabile hemiacetal 7 (FIG. 4), which could in turn be diastereoconvergently deoxycyanated to provide GS-441524.

After investigating distinct approaches, the desired reactivity was achieved by means of a Mn-catalyzed benzylic C—H oxidation. Notably, exclusive reactivity of the α-anomer 5 was observed, most likely resulting from the higher accessibility of its β-hydrogen atom to the Mn-porphyrin complex, in accordance with DFT-optimized ground-state structures (see Supporting Information, Figure S31). Shorter reaction times and portionwise addition of the oxidant are crucial factors determining the chemoselectivity, with fragmentative overoxidation to the ribonolactone being the most prominent side reaction. Starting from peracetylated α-ribonucleoside 6, which was synthesized on a 15 mmol scale in 60% yield from D-ribose with a single purification via column chromatography, oxidation product 7 was obtained as an inconsequential mixture of isomers (equilibrium distribution in $CD_2Cl_2$: 46:54 ketone/hemiacetal, α:β=63:37) in 27% total yield (57% brsm).

Previous reports on the deoxycyanation of the benzyl-protected hemiacetal provided great insight for the final step of our route. Due to the neighbouring acetoxy groups, however, intermediate 7 showed significantly lower reactivity. As a result, the inventors substituted the original mixture of TfOH/TMSOTf with the even stronger Brønsted acid $HNTf_2$, which generates the active Lewis acid TMS-$NTf_2$ in situ upon treatment with TMSCN. In addition, reducing the equivalents of TMSCN prevents further reaction of the product (see Supporting Information, Table S3) and overnight reaction at −40° C. delivered the peracetylated cyanation product in 84% yield and with good diastereoselectivity (α:β=87:13). Notably, GS-441524 precipitated as a single stereoisomer during the subsequent methanolysis in 81% yield, 68% from hemiacetal 7.

EXPERIMENTAL PART

1.1 Arylation of Unprotected Sugars

General Procedure for the Arylation of Unprotected Sugars (1S,2S,3R,4R)-1-(4-aminopyrrolo[2,1-f][1,2,4]triazin-7-yl)pentane-1,2,3,4,5-pentaol, 1

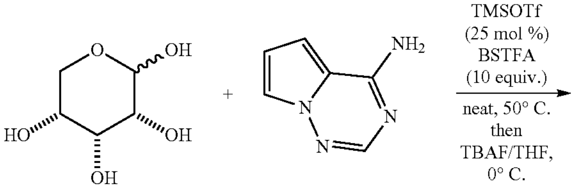

-continued

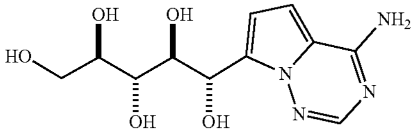

TMSOTf (Trimethylsilyl trifluoromethanesulfonate, 9 μL, 11.1 mg, 50.0 μmol, 0.25 equiv.) was slowly added to a stirred suspension of D-(−)-ribose (30.1 mg, 0.2 mmol, 1.0 equiv.) and pyrrolo[2,1-f][1,2,4]triazin-4-amine (40.3 mg, 0.3 mmol, 1.5 equiv.) in BSTFA (N,O-Bis(trimethylsilyl) trifluoroacetamide, 0.53 mL, 516 mg, 2.0 mmol, 10 equiv.) at room temperature. The mixture was stirred at this temperature for 5 minutes, after which point the solution became homogeneous, and was then heated to 50° C. After 24 hours, thin-layer chromatography (TLC) analysis showed complete consumption of the ribose starting material, at which point the reaction was cooled to room temperature and then to 0° C. A solution of TBAF (Tetrabutylammonium fluoride, 2.2 mL, 1 M in THF, 2.2 mmol, 11 equiv.) was then slowly added and the solution was stirred at this temperature for 2 hours, before concentrating in vacuo. The crude product was purified by column chromatography on silica gel (EtOAc->10% MeOH in EtOAc), to give 1 (48.7 mg, 0.17 mmol, 86%) as a white solid.

HRMS ($ESI^+$) calculated for $C_{11}H_{17}N_4O_5$ $[M+H^+]$ 285.119345, found 285.119410.

Additional Substrates for the Arylation of Unprotected Sugars (1S,2S,3S,4R)-1-(4-aminopyrrolo[2,1-f][1,2,4]triazin-7-yl)pentane-1,2,3,4,5-pentaol, 2

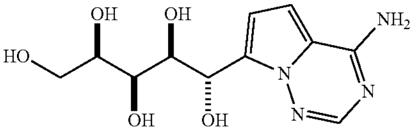 [SMILES: Nc1ncnn2c([C@H](O)[C@H](O)[C@@H](O)[C@H](O)CO)ccc12]

TMSOTf (9 μL, 11 mg, 50 μmol, 0.25 equiv.) was slowly added to a stirred suspension of D-(−)-xylose (45.0 mg, 0.3 mmol, 1.5 equiv.) and pyrrolo[2,1-f][1,2,4]triazin-4-amine (26.8 mg, 0.2 mmol, 1.0 equiv.) in BSTFA (0.53 mL, 516 mg, 2.0 mmol, 10 equiv.) at room temperature. The mixture was stirred at this temperature for 5 minutes, before being heated to 50° C. After 4 days, thin-layer chromatography (TLC) analysis showed complete consumption of the arene starting material, at which point the reaction was cooled to room temperature and then to 0° C. A solution of TBAF (2.2 mL, 1 M in THF, 2.2 mmol, 11 equiv.) was then slowly added and the solution was stirred at this temperature for 2 hours, before concentrating in vacuo. The crude product was purified by column chromatography on silica gel (EtOAc->10% MeOH in EtOAc), to give 2 (30.1 mg, 0.1 mmol, 53%) as an off-white solid.

HRMS ($ESI^+$) calculated for $C_{11}H_{17}N_4O_5$ $[M+H^+]$ 285.119345, found 285.119100.

(1S,2S,3R,4R)-1-(5-bromo-1-methyl-1H-indol-3-yl) pentane-1,2,3,4,5-pentaol, 3

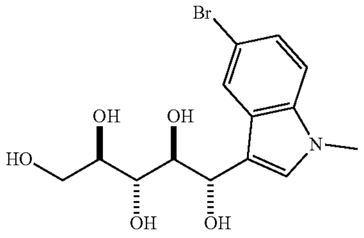 [SMILES: Cn1cc([C@H](O)[C@H](O)[C@H](O)[C@H](O)CO)c2cc(Br)ccc21]

TMSOTf (9 μL, 11 mg, 50 μmol, 0.25 equiv.) was slowly added to a stirred suspension of D-(−)-ribose (45.1 mg, 0.3 mmol, 1.5 equiv.) in BSTFA (0.53 mL, 516 mg, 2.0 mmol, 10 equiv.) at room temperature. The mixture was stirred at this temperature for 5 minutes, after which point the solution became homogeneous, and 5-bromo-1-methyl-1H-indole (42.2 mg, 0.2 mmol, 1.0 equiv.) was added in one portion. The reaction mixture was then kept stirring at room temperature. After 48 hours, thin-layer chromatography (TLC) analysis showed complete consumption of the indole starting material, at which point the reaction was cooled to room temperature and then to 0° C. A solution of TBAF (2.2 mL, 1 M in THF, 2.2 mmol, 11 equiv.) was then slowly added and the solution was stirred at this temperature for 2 hours, before concentrating in vacuo. The crude product was purified by column chromatography on silica gel ($CH_2Cl_2$→10% MeOH in $CH_2Cl_2$; Note: the silica must be pre-treated with a 5% $Et_3N$ in $CH_2Cl_2$ solution prior to chromatography), to give 3 (49.8 mg, 0.1 mmol, 69%) as a white solid.

HRMS ($ESI^+$) calculated for $C_{14}H_{18}NO_5BrNa$ [$M+Na^+$] 382.026068, found 382.026000.

(1S,2S,3R,4R)-1-(2,4,6-trimethoxyphenyl)pentane-1,2,3,4,5-pentaol, 4

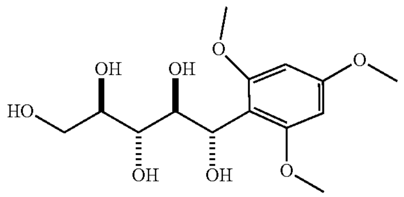

TMSOTf (9 μL, 11 mg, 50 μmol, 0.25 equiv.) was slowly added to a stirred suspension of D-(−)-ribose (44.9 mg, 0.3 mmol, 1.5 equiv.) in BSTFA (1.06 mL, 1.03 g, 4.0 mmol, 20 equiv.) at room temperature. The mixture was stirred at this temperature for 5 minutes, after which point the solution became homogeneous, and 1,3,5-trimethoxybenzene (33.7 mg, 0.2 mmol, 1.0 equiv.) was added in one portion. The reaction mixture was then heated to 50° C. After 48 hours, thin-layer chromatography (TLC) analysis showed complete consumption of the arene starting material, at which point the reaction was cooled to room temperature and then to 0° C. A solution of TBAF (4.4 mL, 1 M in THF, 4.4 mmol, 22 equiv.) was then slowly added and the solution was stirred at this temperature for 2 hours, before concentrating in vacuo. The crude product was purified by column chromatography on silica gel (EtOAc->10% MeOH in EtOAc; Note: the silica must be pre-treated with a 5% $Et_3N$ in EtOAc solution prior to chromatography), to give 4 (45.1 mg, 0.1 mmol, 71%) as a white solid.

HRMS ($ESI^+$) calculated for $C_{14}H_{22}O_8Na$ [$M+Na^+$] 341.120689, found 341.120290.

Divergence of Product Outcome with Different Cyclization Conditions

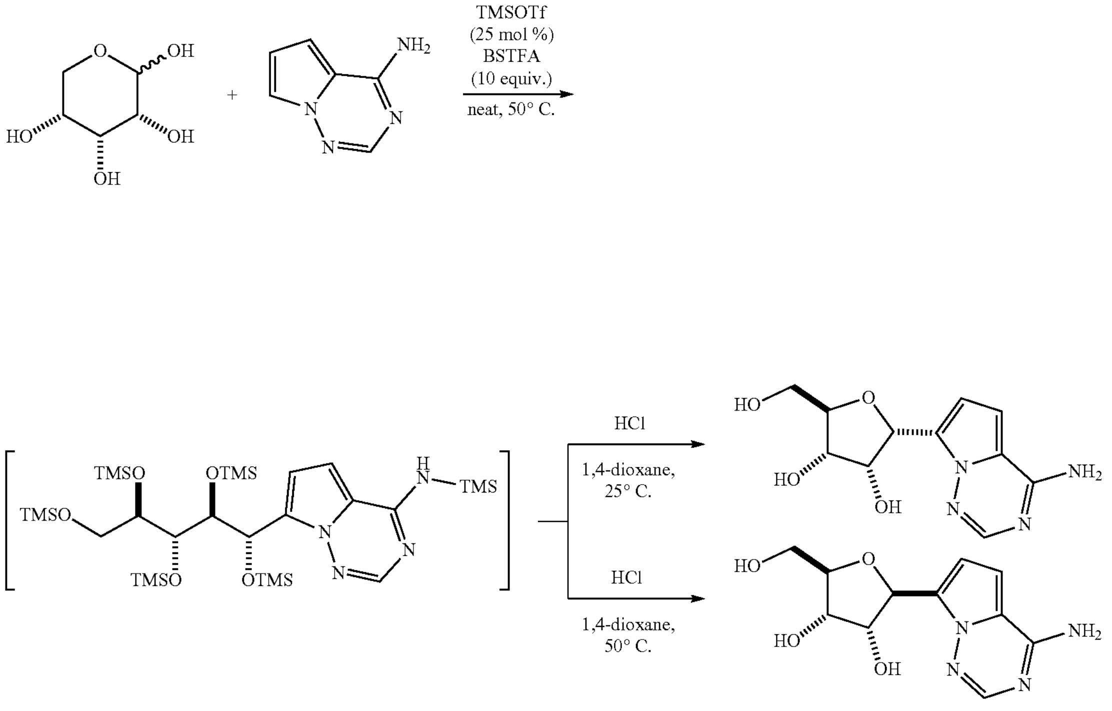

(2R,3R,4S,5R)-2-(4-aminopyrrolo[2,1-f][1,2,4]triazin-7-yl)-5-(hydroxymethyl)tetrahydro-furan-3,4-diol, α-5

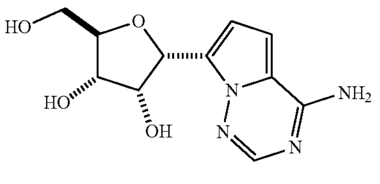 [SMILES: Nc1ncnn2c([C@H]3O[C@H](CO)[C@@H](O)[C@H]3O)ccc12]

TMSOTf (90 μL, 111 mg, 0.5 mmol, 0.25 equiv.) was slowly added to a stirred suspension of D-(−)-ribose (302 mg, 2.0 mmol, 1.0 equiv.) and pyrrolo[2,1-f][1,2,4]triazin-4-amine (326 mg, 2.4 mmol, 1.2 equiv.) in BSTFA (5.0 mL, 4.87 g, 18.9 mmol, 10 equiv.) at room temperature. The mixture was stirred at this temperature for 5 minutes, after which point the solution became homogeneous, and was then heated to 50° C. After 48 hours, thin-layer chromatography (TLC) analysis showed complete consumption of the ribose starting material, at which point the reaction was cooled to room temperature and then to 0° C. A solution of HCl (20 mL, 4 M in 1,4-dioxane, 80 mmol, 40 equiv.) was then slowly added and the suspension was vigorously stirred at this temperature for 10 minutes, before warming to room temperature. After 24 hours, the mixture was diluted with $Et_2O$ (30 mL), filtered over a glass frit, and the solid was washed with $Et_2O$, before drying under vacuum. The crude mixture was then dissolved in MeOH (20 mL) and $NaHCO_3$ (11 g) was added. The mixture was then stirred for 30 minutes before filtering, washing with MeOH, and concentrating in vacuo. The crude product was purified by column chromatography on silica gel (EtOAc->10% MeOH in EtOAc), to give α-5 (377 mg, α/β 9:1, 1.4 mmol, 71%) as an off-white solid.

HRMS ($ESI^+$) calculated for $C_{11}H_{15}N_4O_4$ $[M+H^+]$ 267.108780, found 267.108860.

(2S,3R,4S,5R)-2-(4-aminopyrrolo[2,1-f][1,2,4]triazin-7-yl)-5-(hydroxymethyl) tetrahydrofuran-3,4-diol, β-5

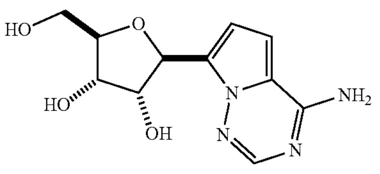 [SMILES: Nc1ncnn2c([C@@H]3O[C@H](CO)[C@@H](O)[C@H]3O)ccc12]

TMSOTf (45 μL, 55.2 mg, 0.25 mmol, 0.25 equiv.) was slowly added to a stirred suspension of D-(−)-ribose (150 mg, 1.0 mmol, 1.0 equiv.) and pyrrolo[2,1-f][1,2,4]triazin-4-amine (202 mg, 1.5 mmol, 1.5 equiv.) in BSTFA (2.6 mL, 2.53 g, 9.84 mmol, 10 equiv.) at room temperature. The mixture was stirred at this temperature for 5 minutes, after which point the solution became homogeneous, and was then heated to 50° C. After 48 hours, thin-layer chromatography (TLC) analysis showed complete consumption of the ribose starting material, at which point the reaction was cooled to room temperature and then to 0° C. A solution of HCl (10 mL, 4 M in 1,4-dioxane, 40 mmol, 40 equiv.) was then slowly added and the suspension was vigorously stirred at this temperature for 10 minutes, before warming to 50° C. After 48 hours, the mixture was cooled to room temperature, diluted with $Et_2O$ (30 mL), filtered over a glass frit, and the solid was washed with $Et_2O$, before drying under vacuum. The crude mixture was then dissolved in MeOH (10 mL) and $NaHCO_3$ (5.5 g) was added. The mixture was then stirred for 30 minutes before filtering, washing with MeOH, and concentrating in vacuo. The crude product was purified by column chromatography on silica gel (EtOAc->10% MeOH in EtOAc), to give β-5 (127.5 mg, α/β 1:6, 0.48 mmol, 48%) as an off-white solid.

HRMS ($ESI^-$) calculated for $C_{11}H_{13}N_4O_4$ $[M-H]^-$ 265.094230, found 265.094460.

Peracetylation of the Ribonucleoside (2R,3S,4R,5R)-2-(4-acetamidopyrrolo[2,1-f][1,2,4]triazin-7-yl)-5-(acetoxymethyl)-tetrahydrofuran-3,4-diyl diacetate, α-6

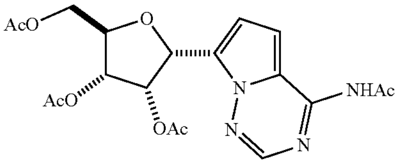 [SMILES: CC(=O)Nc1ncnn2c([C@H]3O[C@H](COC(C)=O)[C@@H](OC(C)=O)[C@H]3OC(C)=O)ccc12]

Nucleoside α-5 (133 mg, 0.5 mmol, 1.0 equiv.) and DMAP (6.1 mg, 50 μmol, 0.1 equiv.) were suspended in triethylamine (0.7 mL, 508 mg, 5.0 mmol, 10 equiv.) at 0° C. Acetic anhydride (0.21 mL, 227 mg, 2.2 mmol, 4.4 equiv.) was then added dropwise and the reaction was warmed to room temperature and stirred for 16 hours. The mixture was diluted with EtOAc and $H_2O$, the organic layer was washed with water (2×), dried over $Na_2SO_4$, and concentrated in vacuo. The crude product was purified by column chromatography on silica gel (1:1 $CH_2Cl_2$/EtOAc), to give α-6 (187 mg, α/β 10:1, 0.4 mmol, 86%) as an off-white solid.

HRMS ($ESI^+$) calculated for $C_{19}H_{22}N_4O_8Na$ $[M+Na^+]$ 457.132984, found 457.133320.

(2S,3S,4R,5R)-2-(4-acetamidopyrrolo[2,1-f][1,2,4]triazin-7-yl)-5-(acetoxymethyl)-tetrahydrofuran-3,4-diyl diacetate, β-6

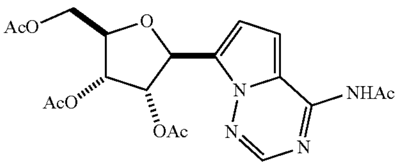 [SMILES: CC(=O)Nc1ncnn2c([C@@H]3O[C@H](COC(C)=O)[C@@H](OC(C)=O)[C@H]3OC(C)=O)ccc12]

Nucleoside β-5 (52.6 mg, 0.2 mmol, 1.0 equiv.) and DMAP (2.4 mg, 20 μmol, 0.1 equiv.) were suspended in triethylamine (275 μL, 200 mg, 2.0 mmol, 10 equiv.) at 0° C. Acetic anhydride (82 μL, 89 mg, 0.9 mmol, 4.4 equiv.) was then added dropwise and the reaction was warmed to room temperature and stirred for 12 hours. The mixture was diluted with EtOAc and $H_2O$, the organic layer was washed with water (2×), dried over $Na_2SO_4$, and concentrated in vacuo. The crude product was purified by column chromatography on silica gel (1:1 $CH_2Cl_2$/EtOAc), to give β-6 (85.8 mg, α/β 1:7, 0.1 mmol, 38%) as an off-white solid.

HRMS ($ESI^+$) calculated for $C_{19}H_{22}N_4O_8$ $[M^+]$ 434.14376, found 434.14360.

Large-Scale/Telescoped Process

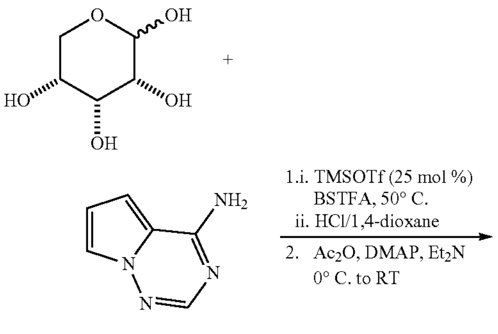

-continued

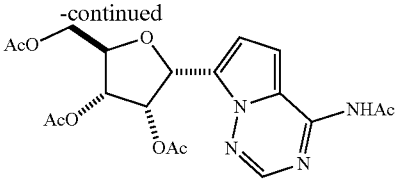

Arylation/Cyclization/Acetylation Sequence on 15 mmol Scale

TMSOTf (0.68 mL, 835 mg, 3.75 mmol, 0.25 equiv.) was slowly added to a stirred suspension of D-(−)-ribose (2.25 g, 15.0 mmol, 1.0 equiv.) and pyrrolo[2,1-f][1,2,4]triazin-4-amine (2.41 g, 18.0 mmol, 1.2 equiv.) in BSTFA (40 mL, 38.6 g, 150 mmol, 10 equiv.) at room temperature. The mixture was stirred at this temperature for 5 minutes, after which point the solution became homogeneous, and was then heated to 50° C. After 60 hours, thin-layer chromatography (TLC) analysis showed complete consumption of the ribose starting material, at which point the reaction was cooled to room temperature and then to 0° C. A solution of HCl (150 mL, 4 M in 1,4-dioxane, 600 mmol, 40 equiv.) was then slowly added and the suspension was vigorously stirred at this temperature for 10 minutes, before warming to room temperature. After 24 hours, the mixture was filtered over a glass frit, and the solid was washed with $Et_2O$, before drying under vacuum. The solid and DMAP (183 mg, 1.5 mmol, 0.1 equiv.) were suspended in triethylamine (22 mL, 16.0 g, 158 mmol, 10 equiv.) at 0° C. Acetic anhydride (6.4 mL, 6.91 g, 67.7 mmol, 4.5 equiv.) was then added dropwise and the reaction was warmed to room temperature and stirred for 16 hours. TLC analysis showed that the reaction was still not complete, so the mixture was cooled to 0° C. once again and additional acetic anhydride (1.4 mL, 1.51 g, 14.8 mmol, 1.0 equiv.) was added. After 6 hours of stirring at room temperature, the mixture was diluted with EtOAc and $H_2O$, the organic layer was washed with water (2×), dried over $Na_2SO_4$, and concentrated in vacuo. The crude product was purified by column chromatography on silica gel (4:3->1:1 $CH_2Cl_2$/EtOAc), to give 6 (3.91 g, α/β 9:1, 9.0 mmol, 60%) as an off-white solid.

General Procedures for the Mn(TPP)-Catalyzed Oxidation of the Ribonucleoside (3R,4R,5R)-2-(4-acetamidopyrrolo[2,1-f][1,2,4]triazin-7-yl)-5-(acetoxymethyl)-2-hydroxytetrahydrofuran-3,4-diyl diacetate, 7

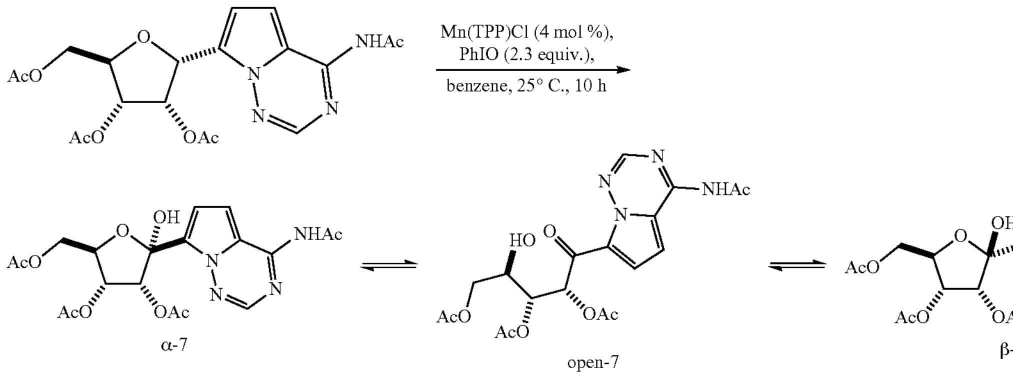

α-7 open-7 β-7

In a flame-dried Schlenk flask at room temperature, Mn(TPP)Cl (4 mol %) and the acetylated ribonucleoside α-6 (1.0 equiv.) were dissolved in freshly degassed benzene (0.05 mol/L). Iodosylbenzene (2.3 equiv. in total, 0.29 equiv. per batch) was added in portions over a period of 8 h (1 h intervals) and, upon complete addition, the reaction mixture was stirred for additional 2 h. The solids were removed by filtration over cotton wool, the solvent was removed under reduced pressure, and the crude product purified by column chromatography on silica gel (1:1->0:1 $CH_2Cl_2$/EtOAc) to give 7 as a mixture of isomers (isomer distribution in $CD_2Cl_2$ open:α:β=46:34:20, 23-32% yield, 50-68% yield based on recovered starting material).

α-7

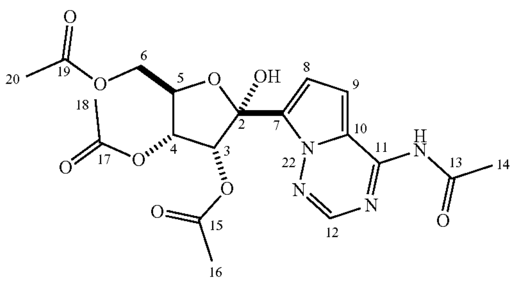

HRMS ($ESI^-$) calculated for $C_{19}H_{21}N_4O_9$ $[M-H]^-$ 449.131405, found 449.131880.

m.p.=60-63° C.

$^1$H NMR (600 MHz, $CD_2Cl_2$) δ 8.28 (s, 1H, NH), 8.15 (s, 1H, $C^{12}H$), 7.08 (d, J=4.8 Hz, 1H, $C^9H$), 6.93 (d, J=4.7 Hz,

1H, $C^8H$), 5.72 (d, J=6.9 Hz, 1H, $C^3H$), 5.37 (dd, J=6.9, 3.8 Hz, 1H, $C^4H$), 4.56 (q, J=3.7 Hz, 1H, $C^5H$), 4.44 (dd, J=12.0, 3.5 Hz, 1H, $C^6H$), 4.27 (dd, J=12.0, 4.7 Hz, 1H, $C^{6'}H$), 2.53 (s, 3H, $C^{14}H_3$), 2.14 (s, 3H, $C^{18}H_3$), 2.07 (s, 3H, $C^{17}H_3$), 2.06 (s, 3H, $C^{20}H_3$).

$^{13}C$ NMR (151 MHz, $CD_2Cl_2$) δ 170.8 ($C^{19}$), 170.7 ($C^{13}$), 170.5 ($C^{17}$), 169.7 ($C^{15}$), 151.3 ($C^{11}$), 146.2 ($C^{12}H$), 129.3 ($C^7$), 116.5 ($C^{10}$), 112.1 ($C^8H$), 104.5 ($C^9H$), 100.5 ($C^2$), 80.4 ($C^5H$), 73.0 ($C^3H$), 70.7 ($C^4H$), 63.7 ($C^6H_2$), 26.0 ($C^{14}H_3$), 21.0 ($C^{20}H_3$), 20.9 ($C^{18}H_3$), 20.7 ($C^{16}H_3$).

β-7

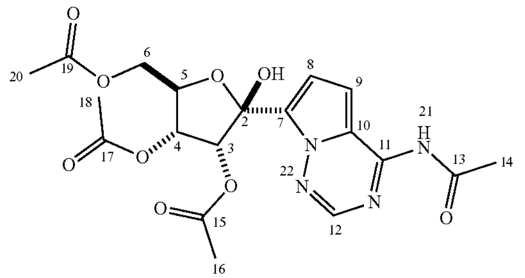

$^1H$ NMR (600 MHz, $CD_2Cl_2$) δ 8.28 (s, 1H, NH), 8.14 (s, 1H, $C^{12}H$), 7.10 (d, J=4.7 Hz, 1H, $C^9H$), 6.97 (d, J=4.7 Hz, 1H, $C^8H$), 5.69 (d, J=4.5 Hz, 1H, $C^3H$), 5.63 (dd, J=7.7, 4.5 Hz, 1H, $C^4H$), 4.53-4.47 (m, 2H, $C^6H$, $C^5H$), 4.27-4.21 (m, 1H, $C^{6'}H$), 2.53 (s, 3H, $C^{14}H_3$), 2.10 (s, 3H, $C^{20}H_3$), 2.03 (s, 3H, $C^{15}H_3$), 1.76 (s, 3H, $C^{16}H_3$).

$^{13}C$ NMR (151 MHz, $CD_2Cl_2$) δ 171.0 ($C^{19}$), 170.7 ($C^{13}$), 170.1 ($C^{17}$), 169.3 ($C^{15}$), 151.2 ($C^{11}$), 146.2 ($C^{12}H$), 128.3 ($C^7$), 116.0 ($C^{10}$), 113.5 ($C^8H$), 104.6 ($C^9H$), 103.6 ($C^2$), 78.8 ($C^5H$), 75.9 ($C^3H$), 72.3 ($C^4H$), 65.1 ($C^6H_2$), 26.0 ($C^{14}H_3$), 21.0 ($C^{20}H_3$), 20.7 ($C^{18}H_3$), 20.5 ($C^{16}H_3$).

open-7

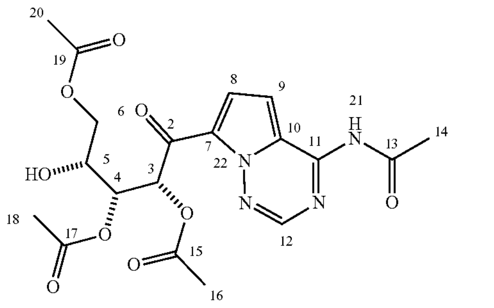

$^1H$ NMR (600 MHz, $CD_2Cl_2$) δ 8.45 (s, 1H, NH), 8.35 (s, 1H, $C^{12}H$), 7.69 (d, J=5.0 Hz, 1H, $C^8H$), 7.13 (d, J=5.0 Hz, 1H, $C^9H$), 6.39 (d, J=3.3 Hz, 1H, $C^3H$), 5.46 (dd, J=7.8, 3.3 Hz, 1H, $C^4H$), 4.31 (bt, J=7.0 Hz, 1H, $C^5H$), 4.19 (dd, J=11.8, 2.8 Hz, 1H, $C^6H$), 4.10 (dd, J=11.8, 6.2 Hz, 1H, $C^{6'}H$), 2.57 (s, 3H, $C^{14}H_3$), 2.21 (s, 3H, $C^{16}H_3$), 2.03 (s, 3H, $C^{18}H_3$), 2.00 (s, 3H, $C^{20}H_3$).

$^{13}C$ NMR (151 MHz, $CD_2Cl_2$) δ 183.0 ($C^2$), 171.3 ($C^{19}$), 171.0 ($C^{13}$), 170.4 ($C^{15}$), 170.1 ($C^{17}$), 151.7 ($C^{11}$), 147.7 ($C^{12}H$), 128.4 ($C^7$), 119.7 ($C^{10}$), 119.6 ($C^8H$), 105.4 ($C^9H$), 76.6 ($C^3H$), 72.0 ($C^4H$), 68.5 ($C^5H$), 65.5 ($C^6H_2$), 26.1 ($C^{14}H_3$), 21.0 ($C^{18}H_3$), 20.9 ($C^{20}H_3$), 20.8 ($C^{16}H_3$).

Procedure for the Cyanation of the Oxidized Ribonucleoside

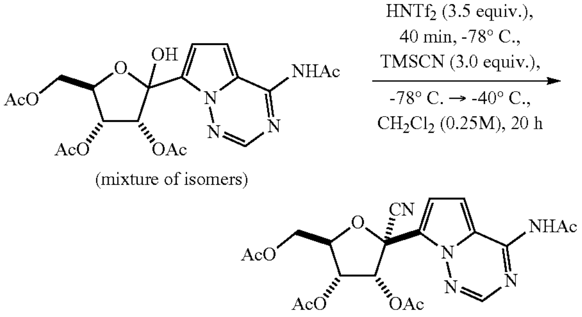

In a flame-dried Schlenk flask under Ar at −78° C., hemiacetal 7 (45.0 mg, 0.10 mmol, 1.0 equiv.) was reacted $HNTf_2$ (0.4 mL, 0.88 mol/L solution in dichloromethane, 0.35 mmol, 3.5 equiv., final reaction concentration 0.25 mol/L) for 40 min. Subsequently, TMSCN (37.5 μL, 29.8 mg, 0.30 mmol, 3.0 equiv.) was added and, after allowing the reaction mixture to warm up to −40° C., stirred for 20 h. The reaction was terminated by the addition of triethylamine (55.8 μL, 40.5 mg, 0.40 mmol, 4.0 equiv.), warmed up to room temperature, and the volatiles were removed under high-vacuum using an additional cooling trap (analysis of an aliquot revealed a diastereomeric mixture of α:β=87:13). The crude reaction mixture was treated with 1.0 mL triethylamine and was directly purified by flash column chromatography on siliga gel (1:1 $CH_2Cl_2$/EtOAc) to provide S4 as an off-white solid (38.5 mg, α:β=89:11, 84%).

(2R,3R,4R,5R)-2-(4-acetamidopyrrolo[2,1-f][1,2,4]triazin-7-yl)-5-(acetoxymethyl)-2-cyanotetrahydrofuran-3,4-diyl diacetate, α-S4

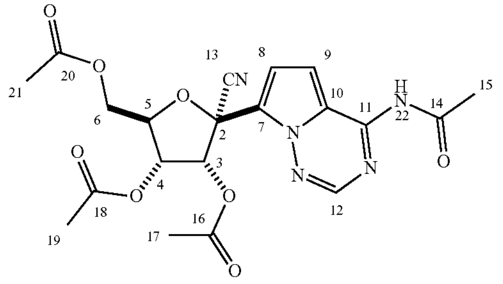 [SMILES: CC(=O)Nc1ncnn2c([C@]3(C#N)O[C@H](COC(C)=O)[C@@H](OC(C)=O)[C@H]3OC(C)=O)ccc12]

HRMS (ESI⁻) calculated for $C_{20}H_{20}N_5O_8$ $[M-H]^-$ 458.131738, found 458.131900.

Procedure for the Deprotection of the Cyanated Ribonucleoside

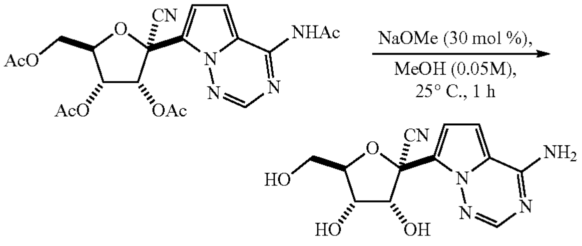

Following a literature-known procedure, (O.-M. Soueidan, B. J. Trayner, T. N. Grant, J. R. Henderson, F. Wuest, F. G. West, C. I. Cheeseman, *Org Biomol Chem* 2015, 13, 6511-6521.) at room temperature compound S4 (54.0 mg, 0.12 mmol, 1.0 equiv., α:β=88:12) in methanol (2.4 mL, 0.05 mol/L) was reacted with NaOMe (8.0 μL, 7.6 mg, 25 wt % in methanol, 0.3 equiv.). After 1 h, precipitation of a white solid was observed, and the solvent was decanted. The precipitate was then treated with additional 1.0 ml of methanol and hexanes, the liquid was decanted, and the solid dried under high-vacuum to provide GS-441524 as a single stereoisomer (27.6 mg, 81%, 92% based on α-S4).

(2R,3R,4S,5R)-2-(4-aminopyrrolo[2,1-f][1,2,4]triazin-7-yl)-3,4-dihydroxy-5-(hydroxymethyl) tetrahydro-furan-2-carbonitrile, GS-441524

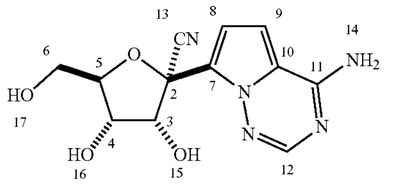

Analytical data is in accordance with literature. (T. Cihlar, S. Bavari et al., *Nature* 2016, 531, 381-385.)

HRMS ($ESI^+$) calculated for $C_{12}H_{14}N_5O_4$ $[M+H]^+$ 292.104028, found 292.103860.

As illustrated above, the inventors have designed and developed a more practical and efficient synthesis of remdesivir starting from free D-ribose. Their route features a novel and completely stereoselective nucleophilic addition of (hetero)arenes to carbohydrates without pre-installation of any protecting or activating groups. The process delivers the linear products via silylium catalysis diastereoselectively due to convergent silylation towards the TMS-protected β-ribopyranose and -furanose prior to the C—C bond formation. The anomeric configuration of the C-nucleoside is tuned simply by means of thermodynamic control during the acid-mediated cyclization. Benzylic C—H oxidation followed by deoxycyanation indeed streamlines the existing chemical synthesis of GS-441524 to just three steps requiring purification from D-ribose and the artificial nucleobase.

The invention claimed is:

1. A process for the glycosylation of an arene comprising reacting a monosaccharide with a silylating agent in the presence of a Lewis acid catalyst and with an aromatic hydrocarbon selected from arenes or heteroarenes, each optionally bearing one or more substituents, and thereby introducing one or more silyl groups to the monosaccharide followed by removing the one or more silyl groups to yield a nucleoside analogue.

2. Process for the glycosylation of an arene according to claim 1, wherein the monosaccharide is selected from tetroses, pentoses, hexoses and any deoxy form thereof.

3. Process for the glycosylation of an arene according to claim 1, wherein the silylating agent is a tri-($C_1$ to $C_6$-alkyl)-substituted silyl compound.

4. Process for the glycosylation of an arene according to claim 1, wherein the aromatic hydrocarbon is selected from arenes or heteroarenes having one to four aromatic or heteroaromatic rings, each optionally being substituted by one or more heterosubstituents.

5. Process for further reacting the glycosylated arene obtained according to the process of claim 1, said process comprising the steps:

a) producing a nucleoside analogue by the process according to claim 1, wherein the monosaccharide is ribose and the heteroarene is pyrrolo[2,1-f][1,2,4]triazin-4-amine;

b) treating the nucleoside analogue with a protecting agent to protect hydroxyl groups of the ribose to thereby obtain a protected nucleoside analogue wherein hydroxyl groups of the ribose are protected with protecting groups;

c) treating the obtained protected nucleoside analogue with an oxidizing agent in the presence of a catalyst to introduce a hydroxyl group on an anomeric carbon atom to obtain a reaction product having a hydroxyl group on the anomeric carbon atom;

d) treating the obtained reaction product having the hydroxyl group on the anomeric carbon atom with a cyanating agent to replace the hydroxyl group on the anomeric carbon atom to thereby obtain a cyanated reaction product; and e) treating the obtained cyanated reaction product with a deprotecting agent to remove the protecting groups from the hydroxyl groups on the ribose.

6. Process according to claim 5, wherein the protecting agent is selected from alkyl halides, alkyl carboxylic acid anhydrides, aryl carboxylic acid anhydrides, alkyl carboxylic acid chlorides, aryl carboxylic acid chlorides, silyl halides, bis(silyl) acetamides, silyl trifluoromethanesulfonates, acetone, alkyl chloromethyl ethers, and 2-(silyl) ethoxy chloromethyl ethers.

7. Process according to claim 5, wherein the oxidizing agent is iodosyl benzene in the presence of the catalyst Mn(TPP)Cl ((5,10,15,20-Tetraphenyl-21H,23H-porphine manganese(III) chloride).

8. Process according to claim 5, wherein the cyanating agent is selected from silyl cyanides, alkali metal cyanides.

9. Process according to claim 5, wherein the deprotecting agent is an alkali alcoholate or alkali carbonate.

10. Process according to claim 2, wherein the monosaccharide is selected from ribose or deoxyribose.

11. Process according to claim 3, wherein the silylating agent is (N,O-Bis(trimethylsilyl)trifluoroacetamide.

12. Process according to claim 6, wherein the protecting agent is acetic anhydride or benzoic anhydride.

13. Process according to claim 8, wherein the cyanating agent is trimethyl silyl cyanide (TMSCN).

14. Process according to claim 9, wherein the deprotecting agent is an alkali alcoholate or alkali carbonate in an aliphatic alcohol.

* * * * *